(12) United States Patent
Voloshin (10) Patent No.: US 11,058,442 B2
(45) Date of Patent: Jul. 13, 2021

(54) DISTAL BICEPS TENDON REPAIR DEVICE

(71) Applicant: University of Rochester, Rochester, NY (US)

(72) Inventor: Ilya Voloshin, Pittsford, NY (US)

(73) Assignee: University of Rochester, Rochester, NY (US)

( * ) Notice: Subject to any disclaimer, the term of this patent is extended or adjusted under 35 U.S.C. 154(b) by 212 days.

(21) Appl. No.: 16/325,387

(22) PCT Filed: Aug. 14, 2017

(86) PCT No.: PCT/US2017/046828
§ 371 (c)(1),
(2) Date: Feb. 13, 2019

(87) PCT Pub. No.: WO2018/035066
PCT Pub. Date: Feb. 22, 2018

(65) Prior Publication Data
US 2019/0192174 A1 Jun. 27, 2019

Related U.S. Application Data

(60) Provisional application No. 62/375,354, filed on Aug. 15, 2016.

(51) Int. Cl.
*A61B 17/17* (2006.01)
*A61F 2/08* (2006.01)
*A61B 17/04* (2006.01)

(52) U.S. Cl.
CPC ........ *A61B 17/1714* (2013.01); *A61F 2/0805* (2013.01); *A61B 17/1739* (2013.01); *A61B 2017/0464* (2013.01)

(58) Field of Classification Search
CPC .......................... A61B 17/1714; A61F 2/0805
See application file for complete search history.

(56) References Cited

U.S. PATENT DOCUMENTS 5,665,096 A * 9/1997 Yoon .................. A61B 17/0469 606/139
5,681,333 A * 10/1997 Burkhart ............ A61B 17/0469 128/898

(Continued)

*Primary Examiner* — Nicholas W Woodall
(74) *Attorney, Agent, or Firm* — Patent Technologies, LLC; Robert D. Gunderman, Jr.

(57) ABSTRACT

A distal biceps tendon repair device is disclosed. The device allows for anatomically correct biceps tendon repair using a single incision anterior approach without the risk associated with a double incision posterior approach. The distal biceps tendon repair device eliminates the necessity of cutting supinator muscle and greatly reduces the risk of contact or damage to vital structures such as arteries or nerves. The device has a bone drill guide mechanically coupled to a cannulated bone hook. A retrieval wire passes through the cannulated bone hook to grasp a suture or suture guide that has passed through a cannulated drill bit retained by the bone drill guide. The retrieval wire brings the suture through the cannulated bone hook, thus bringing the suture through and around the bone for subsequent anatomically correct attachment and placement of sutures used to reattach the distal biceps tendon to the bone.

19 Claims, 11 Drawing Sheets (56) References Cited

U.S. PATENT DOCUMENTS

| | | | | |
|---|---|---|---|---|
| 6,723,107 B1 * | 4/2004 | Skiba | ............... | A61B 17/0469 |
| | | | | 606/144 |
| 8,523,872 B2 * | 9/2013 | Ek | ................ | A61B 17/1675 |
| | | | | 606/96 |
| 9,463,012 B2 * | 10/2016 | Bonutti | ............ | A61B 17/0482 |
| 9,782,165 B2 * | 10/2017 | Murphy | ............ | A61B 17/0469 |
| 2011/0009867 A1 * | 1/2011 | Oren | ............... | A61B 17/0482 |
| | | | | 606/80 |

* cited by examiner

DISTAL BICEPS TENDON REPAIR DEVICE

CROSS REFERENCE TO RELATED PATENT APPLICATIONS

This application claims priority to U.S. Patent Application Ser. No. 62/375,354 filed Aug. 15, 2016 entitled "Distal Biceps Tendon Repair Device" by Dr. Ilya Voloshin, M.D., and to International Application Number PCT/US17/46828 filed Aug. 14, 2017, the entire disclosures of which are incorporated herein by reference in their entirety.

BACKGROUND OF THE INVENTION

1. Field of the Invention

This invention relates generally to musculoskeletal repair, and more specifically to a device that assists a surgeon in distal biceps tendon repair surgery using an anterior incision that provides optimal tendon reattachment with minimal loss of supination strength and less risk to the posterior interosseous nerve.

2. Description of Related Art

To regain use distal biceps tendon tears need to be repaired in patients who are not sedentary. There are currently two main surgical approaches to distal biceps tendon repair. There is a one incision anterior approach (AA) and a two incision posterior at (PA). AA is a single incision surgical approach which is less invasive than the two incision posterior approach, and is more cosmetic as well. While post-operative cosmetic appearance may have importance among some patients, a more clinically important reason to perform one incision anterior approach is that of less risk of heterotopic ossification and no trauma to the supinator muscle. While a two incision posterior approach has been shown to provide equally good overall one, term strength and range of motion and use, it involves cutting of muscles to access the repair site and involves cutting of the supinator muscle. Therefore, while the two incision posterior approach allows anatomically correct repair and provides a superior mechanical attachment technique to that of the one incision anterior approach, it involves the downside of two incisions, increased risk of heteropic ossification and damage to the supinator muscle; a procedure that many surgeons are reluctant to undertake. Therefore, anterior single incision surgeries are much more commonplace, there is not a device currently available to allow for perfect anatomical repair of distal biceps tendons without the downside of the PA (two incision) approach. The anatomic repair technique and placement of the reattachment point seems to make a difference in supination strength when the forearm is in 60 degrees of supination. About 33% loss of supination strength occurs when the forearm is in a 60 degree of supination position. One may argue how important this loss of strength really is. Most activities probably would not be affected by loss of this amount of strength in this position. However, heavy laborers or athletes most likely will notice the difference. The two incision posterior approach (PA) is a more invasive procedure than the single incision anterior approach. For example, the surgeon must cut supinator muscle to get access to the repair site in order to reattach the tendon; but it allows for perfect anatomic repair. Both the non-anatomic repair that is typically performed with the one incision anterior approach as well as the anatomic repair that is typically performed with the two incision posterior approach result in decrease in muscle strength after surgery; the former approach due to non-anatomic reattachment of the tendon and the latter approach due to cutting of the supinator muscle. Even with the loss of muscle strength associated with cutting the supinator muscle in anatomic repair, the benefit in recovery strength of anatomic repair seems to outweigh the downside of cutting supinator muscle. Due to increased risk of heterotopic ossification and damage to supinator muscle, anatomic repair using a two incision posterior approach is still a risky procedure, and one that many surgeons shy away from in favor of the non-anatomic single incision anterior approach.

What is therefore needed is a device to enable a surgical technique for distal biceps tendon repair that is anatomical and uses an anterior single incision approach to eliminate the necessity of cutting supinator muscles while minimizing risk of damage to vital structures. Such a device would revolutionize the field of biceps tendon reattachment surgery. The details of such a novel device are therefore presented herein.

BRIEF SUMMARY OF THE INVENTION

In accordance with the present invention, there is provided a device for distal biceps tendon repair that comprises a guide assembly mechanically coupled to a cannulated bone hook; the cannulated bone hook configured to accommodate movement of a retrieval wire; and a bone drill stop at the distal end of the cannulated bone hook.

In one embodiment, the device for distal biceps tendon repair comprises a guide assembly comprising a proximal end, a distal end, a bone drill guide and a retrieval wire guide; a cannulated hone hook comprising a distal end, a proximal end and a hollow interior; the distal end of the guide assembly formed with the proximal end of the cannulated one hook; the bone drill guide of the guide assembly having an entry at the proximal end of the guide assembly and an exit where the distal end of the guide assembly forms with the proximal end of the cannulated bone hook; the bone drill guide of the guide assembly capable of receiving a bone drill; the cannulated bone hook having a hollow interior that connects with the retrieval wire guide of the guide assembly to allow passage of a retrieval wire; and a bone drill stop at the distal end of the cannulated bone hook.

The foregoing paragraph has been provided by way of introduction, and is not intended to limit the scope of the invention as described in this specification and the attached drawings and claims.

BRIEF DESCRIPTION OF THE DRAWINGS

The invention will be described by reference to the following drawings, in which like numerals refer to like elements, and in which.

The present invention will be described as connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification and the attached drawings and claims.

DESCRIPTION OF THE PREFERRED EMBODIMENTS

For a general understanding of the present invention, reference is made to the drawings. In the drawings, like reference numerals have been used throughout to designate identical elements.

The present invention will be described by way of example, and not limitation. Modifications, improvements and additions to the invention described herein may be determined after reading this specification and viewing the accompanying drawings; such modifications, improvements, and auditions being considered included in the spirit and broad scope of the present invention and its various embodiments described or envisioned herein.

The distal biceps tendon repair device allows for the repair and anatomically correct reattachment, repair and healing of a distal biceps tendon tear using a single incision anterior surgical approach. Such an approach provides for superior supination strength post-surgery due to the tendon reattachment point used, while reducing the risk associated with a posterior surgical approach that has heretofore been the only approach that has been possible with this preferred biceps tendon reattachment point. The distal biceps tendon repair device of the present invention therefore allows for the reattachment of a torn biceps tendon to its posterior anatomic insertion site with a safer anterior surgical incision, something heretofore not possible without posterior incision and the associated risks thereof.

The distal biceps tendon repair device provides for accurate bone drilling and the ability to guide sutures around the back side (posterior side) of the radial tuberosity. The radial tuberosity is an oval projection from the medial surface at the radius, beneath the neck of the radius, gives attachment to the tendon of the biceps (the biceps brachii tendon) on its posterior half. The reattachment point of the biceps brachii tendon that is possible with the distal biceps tendon repair device of the present invention is anatomically correct, thus providing for improved supination strength post surgery compared with current traditional reattachment methods.

Figure 1:
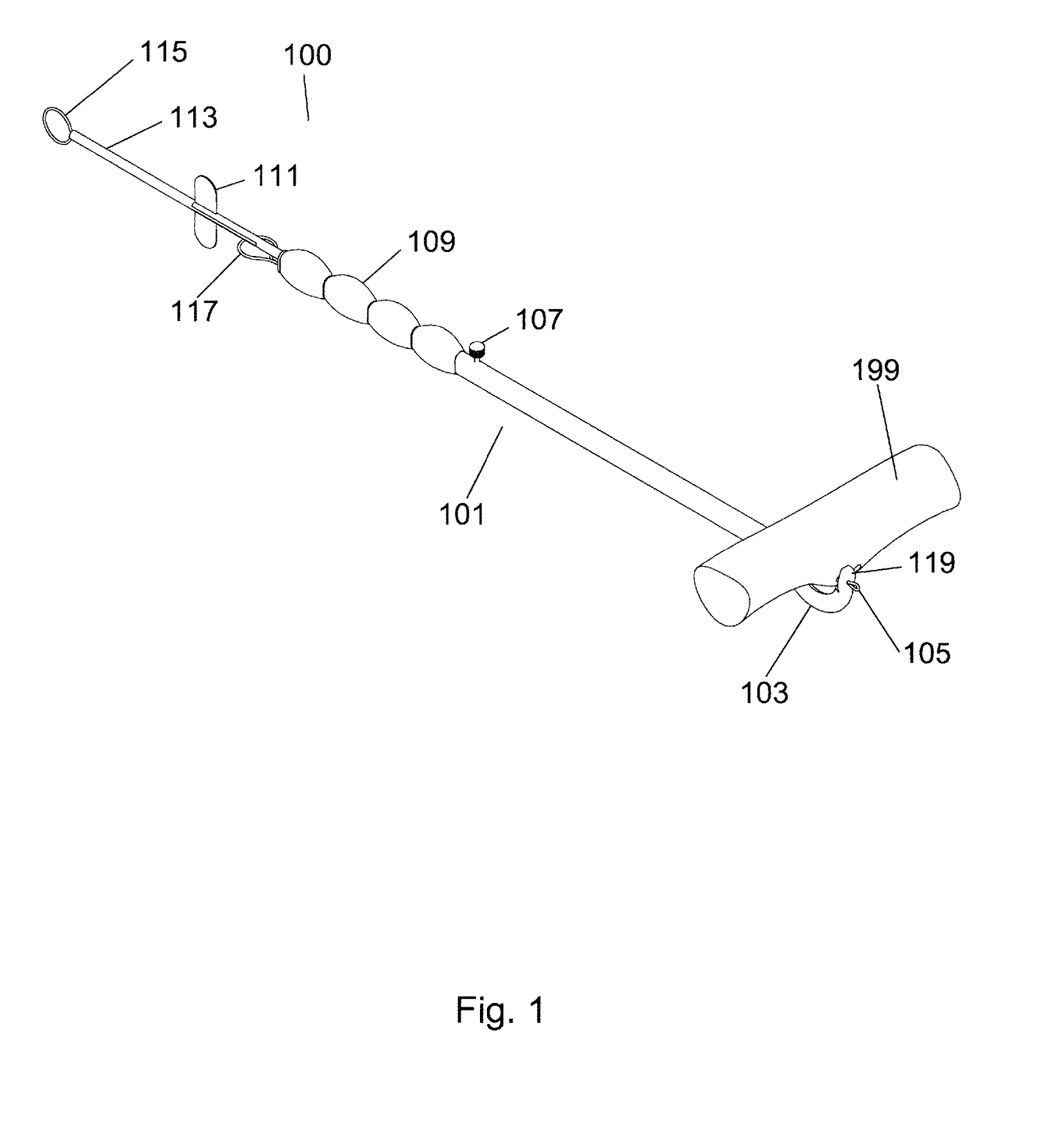
FIG. 1 is a perspective view of the distal biceps tendon repair device in use.

Referring to the present invention in detail, in FIG. 1 there is shown a side plan view of the distal biceps tendon repair device 100. The device may be made of various surgically acceptable materials such as for example, stainless steel, tantalum, cobalt chromium, nitinol, polymers, or the like. Manufacturing techniques of the components of the distal biceps tendon repair device 100 include machining, extruding, casting, forming, pressing, molding, assembly, and the like.

Figure 4A:
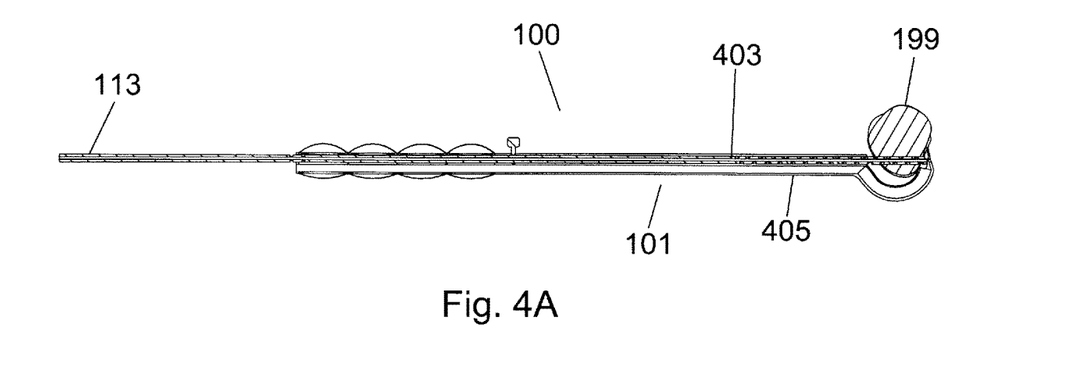
FIGS. 4A-4C depict cross sectional views of the distal biceps tendon repair device in use, each taken along line A-A of FIG. 3.
Figure 4B:
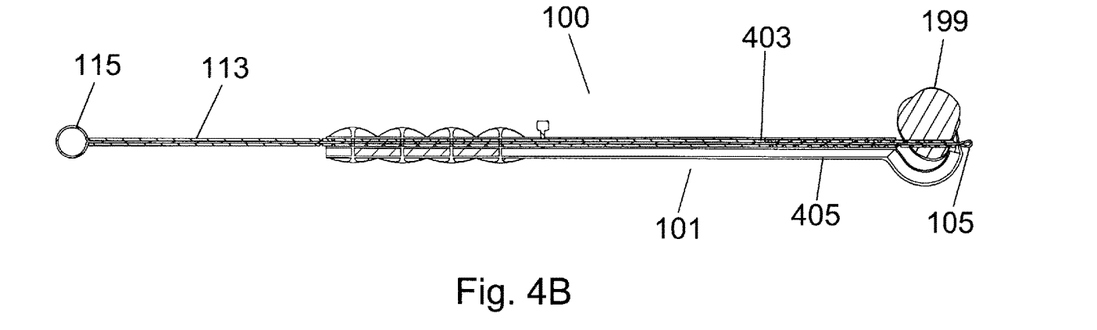
Figure 4C:
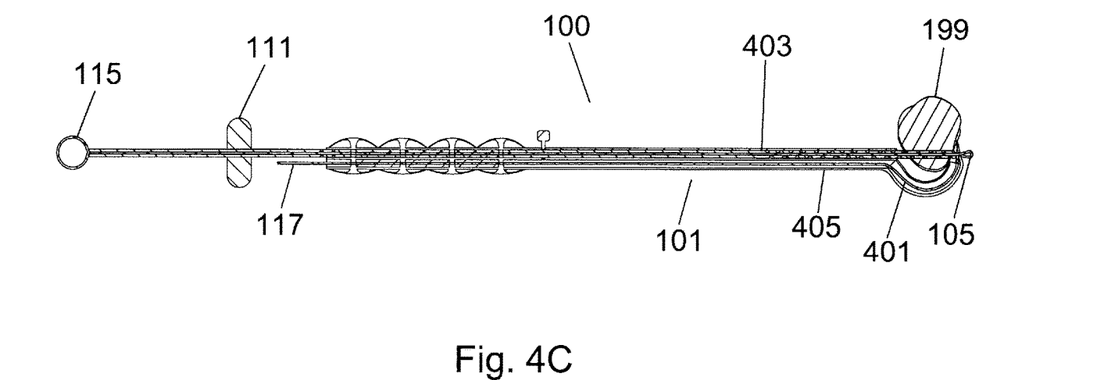

The distal biceps tendon repair device 100 comprises a guide assembly 101 which is mechanically coupled or otherwise formed with a cannulated bone hook 103. The cannulated bone hook 103 and guide assembly are configured to accommodate movement of a retrieval wire in a hollow or open passageway. A bone drill stop 119 can be seen in FIG. 1 at the distal end of the cannulated bone hook 103. The guide assembly 101 has two passageways or cannulas, one for the placement of a cannulated drill bit and the other for placement and movement of a retrieval wire. The guide assembly 101 has a proximal end (the end the surgeon grasps) and a distal end (the end closer to the patient). The two passageways are referred to as a bone drill guide and a retrieval wire guide. A cross section of the guide assembly 101 can be seen in FIGS. 4A, 4B and 4C showing each of these passageways. The cannulated bone hook 103 continues the cannula of the guide assembly 101 that allows for movement of a retrieval wire. The cannulated bone hook 103 is shaped as a hook or a j-like structure that allows for placement around the radius and the related radial tuberosity to allow for the anatomically correct reattachment of the distal biceps tendon. The cannulated one hook 103 ends with a bone drill stop 119 that is concavely shaped to receive the cannulated drill bit 113, and in some embodiments has a gradual taper or rounded point or tip to allow for the efficient and safe placement of the cannulated bone hook 103 around the radius. The cannulated bone hook 103 has a distal end with a bone drill stop and a proximal end. The cannulated bone hook 103 has a hollow interior. The distal end of the guide assembly 101 is formed or otherwise attached to the proximal end of the cannulated bone hook 103 to form a passageway for guiding a retrieval wire. In some embodiments of the present invention a small hole is located toward the center or slightly offset in the bone drill stop 119 to allow a suture or suture loop 105 to pass through the hole to facilitate capture of the suture or suture loop 105 by a retrieval wire and appendage that travels through the cannulated bone hook 103 as seen in FIG. 4C.

The bone drill guide of the guide assembly has an entry at the proximal end of the guide assembly 101 and an exit where the distal end of the guide assembly forms with the proximal end of the cannulated bone hook 10. The bone drill guide is thus capable of receiving a bone drill such as a cannulated drill bit 113.

Thus, a drill bit such as a cannulated drill bit 113 is placed through the guide assembly 101. A manual drill bit extractor 111 has a sleeve or other similar structure that fits within the guide assembly 101 and the cannulated drill bit 113 is then placed within the sleeve (see FIG. 13 for a view of the sleeve and extractor component). The manual drill bit extractor sleeve is then extended forward onto the radius with force that is determined by the surgeon, and a set screw or other retention device 107 that is mechanically engaged with the guide assembly 101 provides pressure on the extractor sleeve, thus acting to clamp the distal biceps tendon repair device 100 onto the radius for further surgical procedures.

The cannulated drill bit 113 is then engaged with a surgical drill and a hole (bone tunnel) made through the radius for biceps tendon reattachment. Once the cannulated drill bit 113 travels through the radius, the bone drill stop 119 prevents further drill bit travel that would surely cause complications and damage. Once the drill is removed from the cannulated drill bit 113 (during the surgical procedure, the cannulated drill bit 113 is left in the distal biceps tendon repair device and the radius itself), a suture, wire, fiber, or similar item is placed through the cannulated drill bit 113, down through the drill bit, through the radius, and out the hole in the bone drill stop 119. Often a suture loop 105 is made on one end of the suture and a suture pull 115 such as a ring, a handle, a loop, a knot, or the like is attached to or made part of the other end (the surgeons or operative end). The suture may be a predetermined length to allow for the exact deployment of the suture through the hole of the bone drill stop 119 but not so far as to cause damage. Once the suture is placed through the cannulated drill bit 113 and radius 199, a retrieval wire (only the retrieval wire pull 117 can be seen in FIG. 1, see FIG. 4C for a view of the retrieval wire 401) is placed through the other passageway (the retrieval wire guide 405 as seen in FIG. 4A) and fed down through the bone retrieval wire guide in the cannulated bone hook 103 at a precise distance (as determined by the length of the retrieval wire and markings on the retrieval wire). At the distal end of the retrieval wire is a grasping or securing appendage that grasps the suture such that the surgeon can then extract the retrieval wire using the pull 117 and also bring the suture out from the guide, thus completing the passage of the suture through the radius 199 and around the posterior side. The suture is now ready to retain a properly prepared biceps tendon for reattachment.

In some embodiments of the present invention, additional features such as grips 109 may be incorporated with the present invention to further facilitate surgical ease or to accomplish specialized, unique or rare procedures, situations or surgical challenges.

With the remaining figures and further explanation thereof, the distal biceps tendon repair device and the surgical techniques that the device enables will become further evident and will enable one skilled in the art to make and use the present invention and the various embodiments described or envisioned herein.

Figure 2:
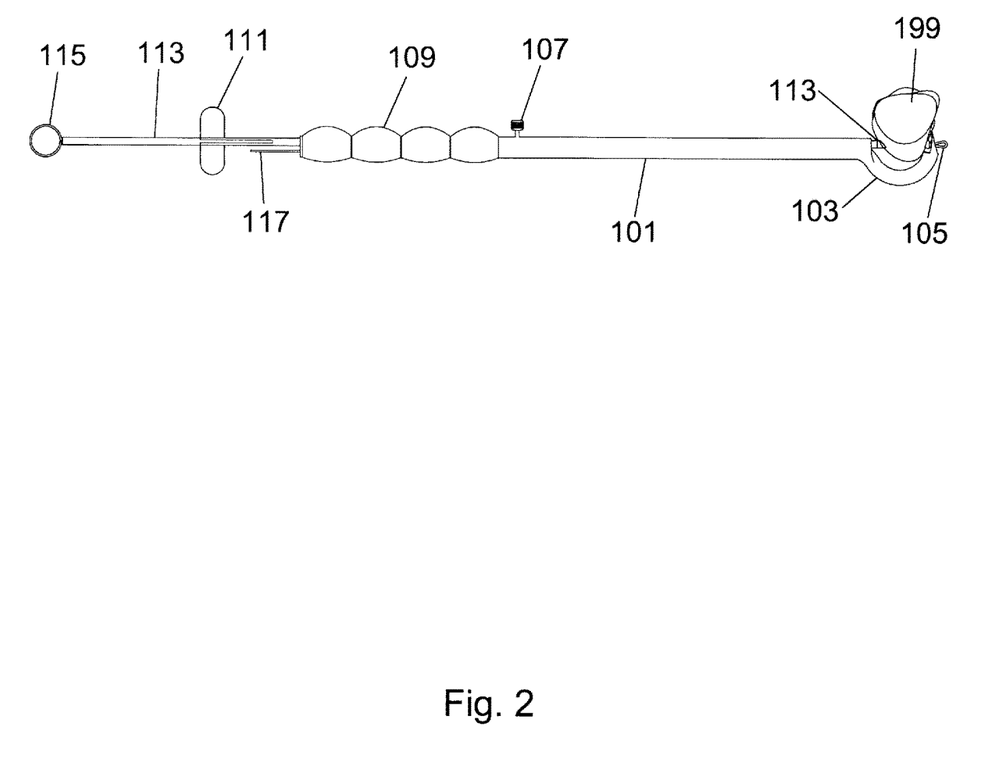
FIG. 2 is a side plan view of the distal biceps tendon repair device in use.

FIGS. 2-8 depict various views of the overall distal biceps tendon repair device. FIG. 2 is a side plan view of the distal biceps tendon repair device in use. One can see how the cannulated drill bit 113 travels through the radius 199 of the patient and the overall device is clamped onto the radius using the manual drill bit extractor sleeve to apply pressure and fixation to the radius 199. The manual drill bit extractor sleeve 1301 can be seen in FIG. 13, and can also be seen near the callout for 113 in FIG. 2 with the cannulated drill bit 113 placed within the sleeve which is in turn within the guide assembly 101, and more particularly the bone drill guide 403 as seen in FIG. 4A-4C. In FIG. 1, the suture has been placed through the cannulated drill bit 113 and has been fully inserted such that the suture loop 105 is slightly protruding from the bone drill stop.

Figure 3:
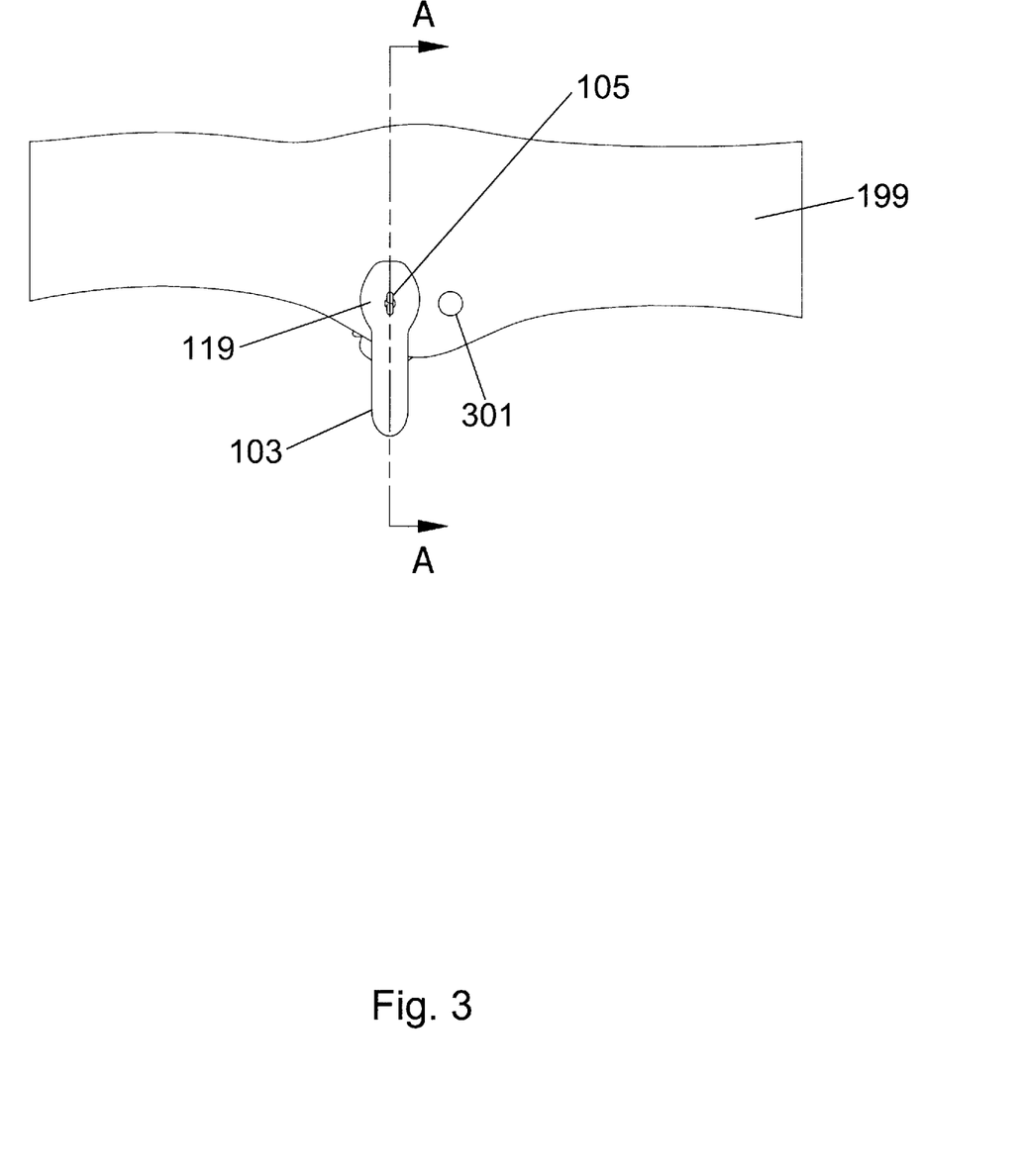
FIG. 3 is a distal end plan view of the distal biceps tendon repair device in use.

FIG. 3 is a distal end plan view of the distal biceps tendon repair device in use where the radius bone has been drilled, the drill removed from the cannulated drill bit 113, and a suture inserted through the cannulated drill bit 113 and out the bone drill stop 119. In some embodiments of the present invention, an adjacent hole 301 or holes may be drilled through the radius bone to provide further tendon repair attachment points. In addition, in some embodiments of the present invention, two or more distal biceps tendon repair devices 100 may be coupled or otherwise connected together at a predetermined distance (for example, spacing between bone tunnels of 5-10 millimeters in one embodiment) to facilitate ease of drilling two or more holes through the radius 199 and subsequent placement of sutures and reattachment of tendon. Of course such an arrangement may have a reduced number of constituent components or additional components and features to allow for such a configuration.

FIGS. 4A-4C depict cross sectional views of the distal biceps tendon repair device in use, each taken along line A-A of FIG. 3. In FIG. 4A, one can clearly see the two passageways that make up the guide assembly 101; that of the bone drill guide 403 and the retrieval wire guide 405. The bone drill guide 403 allows a surgeon to pass a cannulated drill bit 113 from the proximal end of the device and out the distal end of the device where in use the device straddles or is otherwise placed around the radius bone 199 of the patient and as the cannulated drill bit 113 exits the distal end of the device it encounters the radius bone 199 and makes an appropriately sized bone tunnel or tunnels for tendon reattachment. The retrieval wire guide 405 can also be seen running parallel with the bone drill guide 403 and then continuing on through the cannulated bone hook 103 before ending adjacent to the bone drill stop 119. FIG. 4A depicts the cannulated drill bit 113 through the radius 199 and with the sleeve in place to secure the overall device to the radius bone 199 through appropriate extension and retention thereof. Next, FIG. 4B depicts the suture fully inserted through the cannulated drill bit 113 with the suture pull 115 in place and the suture loop 105 extending or partially extending through the hole in the bone drill stop 119. Now to retrieve the distal end of the suture (the suture loop end 105) and bring it around the circumference of the radius 199, a retrieval wire 401 is placed down the retrieval guide 405 and around the bend in the cannulated one hook 103 where it exits the guide and an attached grasping appendage (as will be further described herein) is used to grasp and retain the suture near the proximal end (the suture loop end 105) for subsequent extraction from the retrieval guide 405, thus accomplishing the task of placing the suture through the created bone tunnel in the radius 199 and circumferentially around the radius 199 for attachment and securement of the distal biceps tendon.

Figure 5:
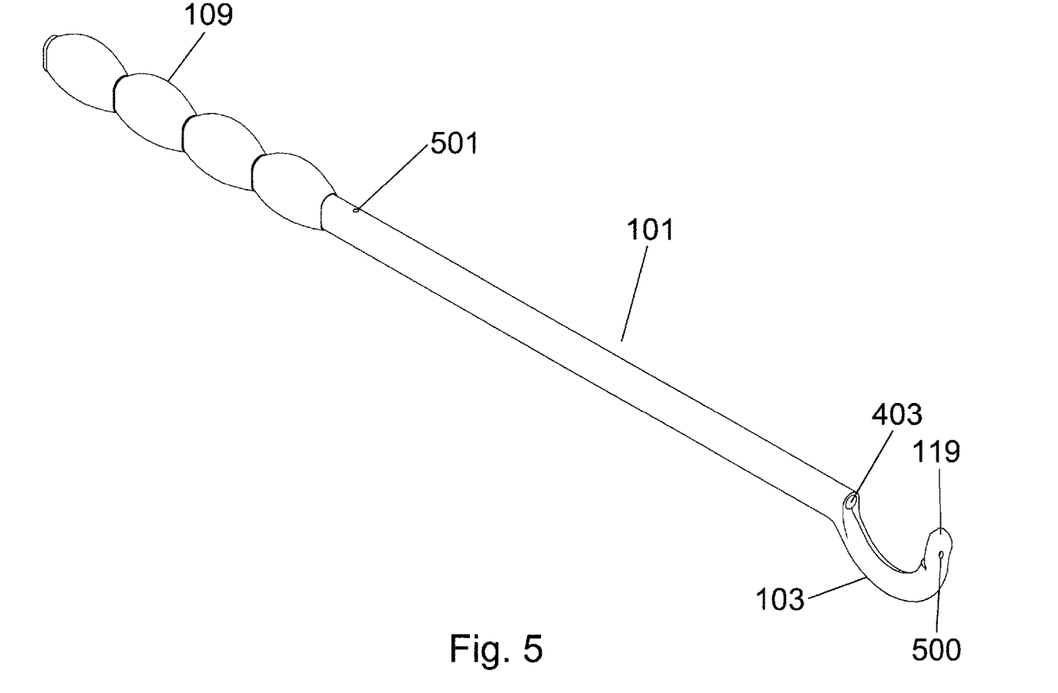
FIG. 5 is a perspective view of the distal biceps tendon repair device.

FIG. 5 is a perspective view of the distal biceps tendon repair device without any related components. The hole in the bone drill stop 119 that creates a suture passageway 500 can be seen along with the set screw port 501 that may be threaded or otherwise contain a retaining structure for the set screw 107 (see FIG. 1) or similar such apparatus that is capable of retaining the manual drill bit extractor sleeve when extended against the radius bone.

Figure 6:
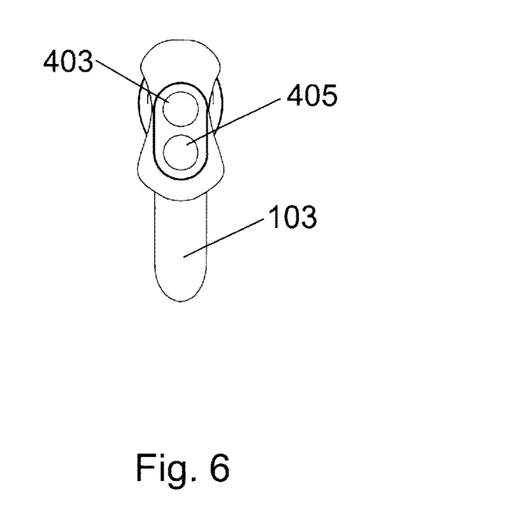
FIG. 6 is a proximal end plan view of the distal biceps tendon repair device.

FIG. 6 is a proximal end plan view of the distal biceps tendon repair device where both the bone drill guide 403 and the retrieval wire guide 405 can be seen making up the guide assembly 101 as seen in FIG. 5, for example.

Figure 7:
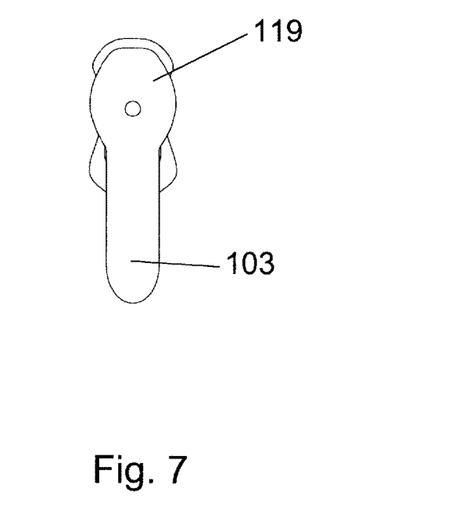
FIG. 7 is a distal end plan view of the distal biceps tendon repair device.

FIG. 7 is a distal end plan view of the distal biceps tendon repair device where the bone drill stop 119 can be seen with the suture passageway 500 and the cannulated bone hook 103. In some embodiments of the present invention, the suture passageway 500 may be of a different geometry or may be absent altogether.

Figure 8:
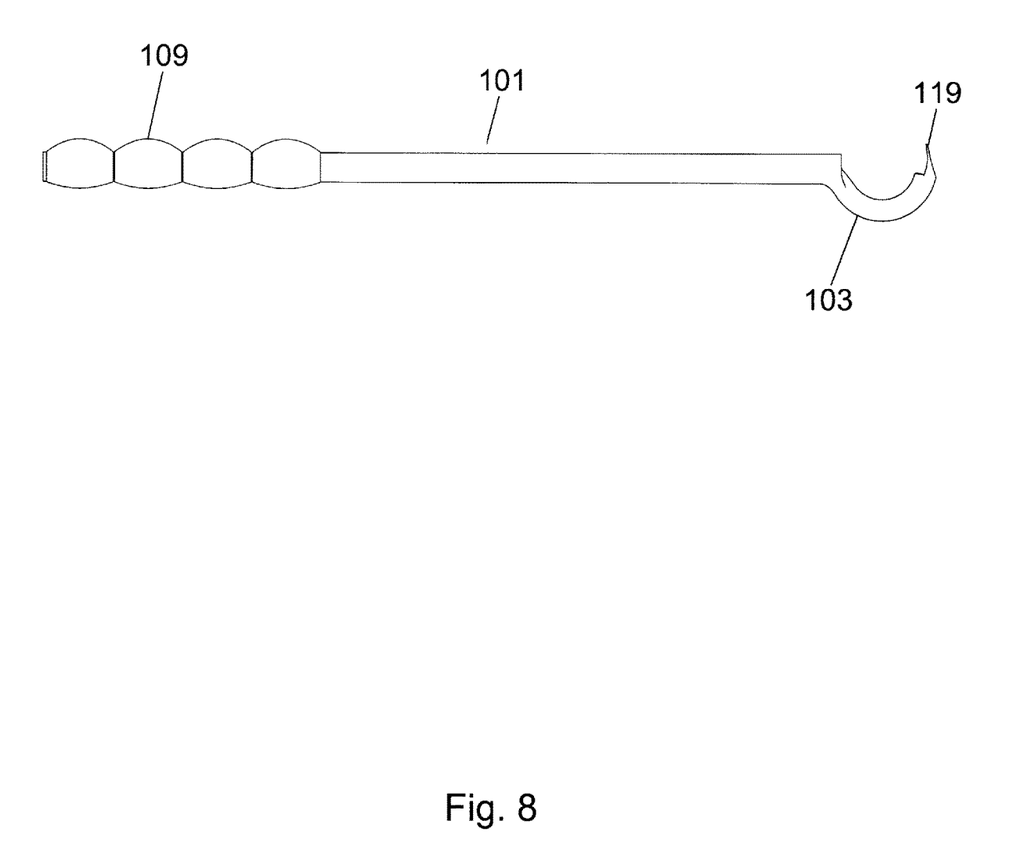
FIG. 8 is a side plan view of the distal biceps tendon repair device.

FIG. 8 is a side plan view of the distal biceps tendon repair device without any related components. From this view, one can see how the retrieval wire guide exits near the bone drill stop 119 and the bone drill guide exits in a generally tangential direction to the opening in the cannulated bone hook where the radius is retained.

Figure 9:
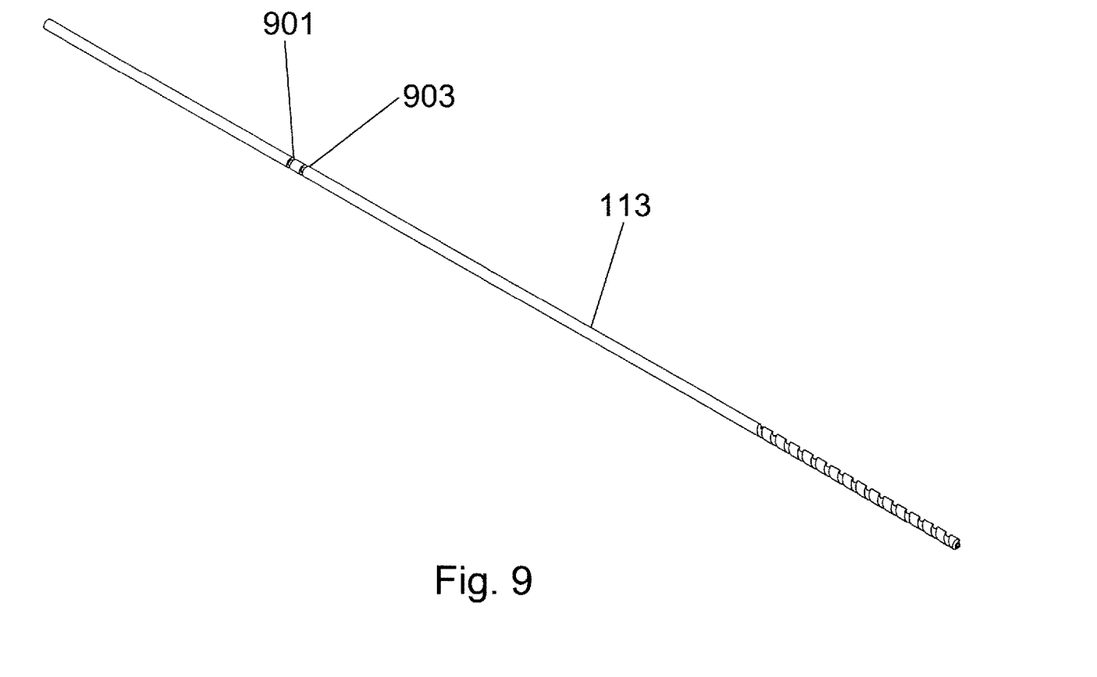
FIG. 9 is a perspective view of the cannulated drill bit of the distal biceps tendon repair device.

A cannulated drill bit 113 can be seen in FIG. 9 in perspective view. While the distal biceps tendon repair that is made possible by the device of the present invention may use a cannulated or a non-cannulated bone drill to create the bone tunnels necessary for subsequent surgical procedures and repair, a cannulated bone drill maintains patency of the tunnel through the radius without the risk of tunnel collapse due to bone or tissue fragments collapsing or otherwise occluding the bone tunnel. A clear passage through the radius is necessary for passing a suture or the like through the bone tunnel and then circumferentially around the radius. A cannulated bone drill thus is a preferred, although not necessary, component of the present invention described herein. A first marker 901 and a second marker 903 can be seen to indicate to the surgeon when the cannulated drill bit 113 has reached the bone drill stop 119 (first marker 901). Once the cannulated drill bit 113 has reached the bone drill stop 119, the surgeon then backs out the cannulated drill bit 113 until the second marker 903 is visible, thus indicating that the cannulated drill bit 113 is slightly removed from the bone drill stop 119, allowing for the exposure and subsequent retention of the suture after it is inserted in the drill bit cannula.

Figure 10:
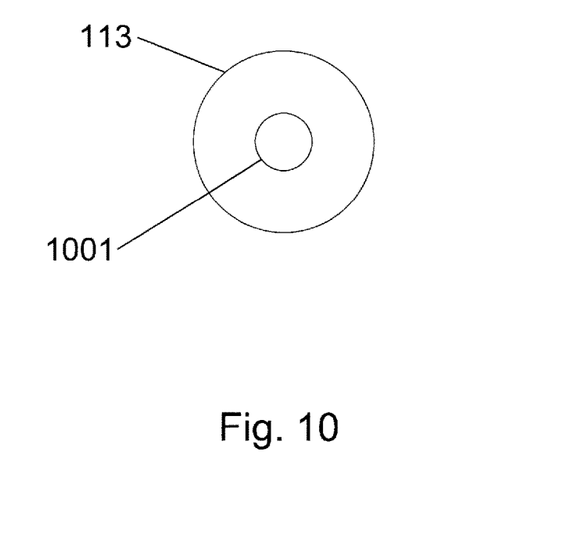
FIG. 10 is an end view of the cannulated drill bit of FIG. 9.

FIG. 10 is an end view of the cannulated drill bit 113 of FIG. 9 showing the cannula 1001. The diameter of the cannulated drill bit being in the range of 1 to 6 millimeters, with 3 millimeters being a preferred value in many procedures.

Figure 11:
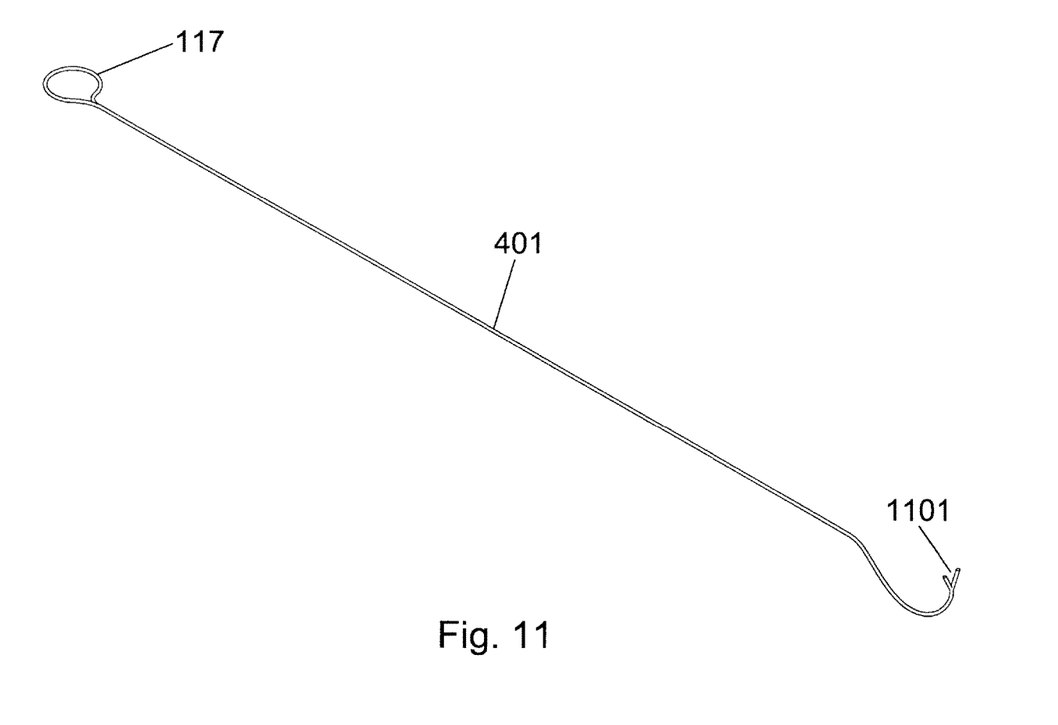
FIG. 11 is a perspective view of the retrieval wire of the distal biceps tendon repair device.

FIG. 11 is a perspective view of the retrieval wire 401 of the distal biceps tendon repair device. The retrieval wire 401 may in fact be a wire such as a stainless steel or nitinol wire, or may, in some embodiments of the present invention, be a polymer or a plastic such as, for example, a monofilament or polyfilament structure. As previously described, the retrieval wire 401 may have a retrieval wire pull 117 or similar structure to assist the surgeon in pulling the retrieval wire 40 out of the guide assembly 101 (specifically the retrieval wire guide 405). Also depicted in FIG. 11 is a retrieval appendage 1101 that may for example be a hook, a claw, or a Y or J shaped appendage. The Y shaped appendage that is depicted in FIG. 11 may be forced together in a closed position as it travels through the constraints of the retrieval wire guide 405 and will open into a Y type shape as it leaves the retrieval wire guide distal end to grasp the suture that has been placed. The branches of the Y appendage open up on either side of the suture, and then when the surgeon draws the retrieval wire 401 back through the constraints of the retrieval wire guide 405 the Y shaped retrieval appendage 1101 closes around and pinches or otherwise grasps or clamps the suture for travel out of the retrieval wire guide. As one can envision, other geometries of the appendage are also possible, and frictional or relief features on the retrieval appendage may improve the functionality of the retrieval appendage or provide functionality that may be beneficial for certain procedures or the like.

Figure 12:
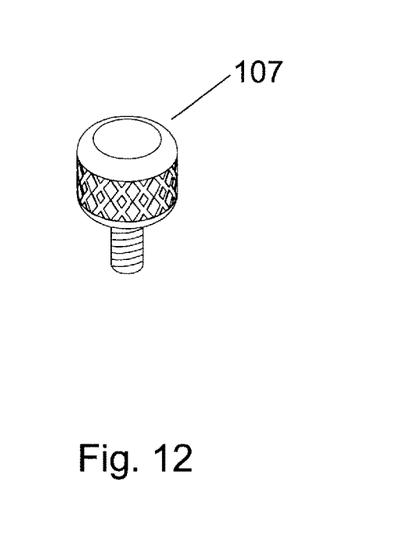
FIG. 12 is a perspective view of the set screw of the distal biceps tendon repair device.

FIG. 12 is a perspective view of the set screw 107 of the distal biceps tendon repair device. The set screw 107 provides downward pressure onto the sleeve 1301 (see FIG. 13) that is inserted in the guide assembly 101 and extended onto the radius bone in a clamping manner while the distal biceps tendon repair device 100 is in use. The set screw 107 is threaded to mate with the set screw port 501 as seen in FIG. 5. Of course other mechanical coupling arrangements can also be employed to facilitate pressure and retention of the sleeve 1301 in an extended position within the guide assembly 101 (more specifically the bone drill guide 403 within the guide assembly 101).

Figure 13:
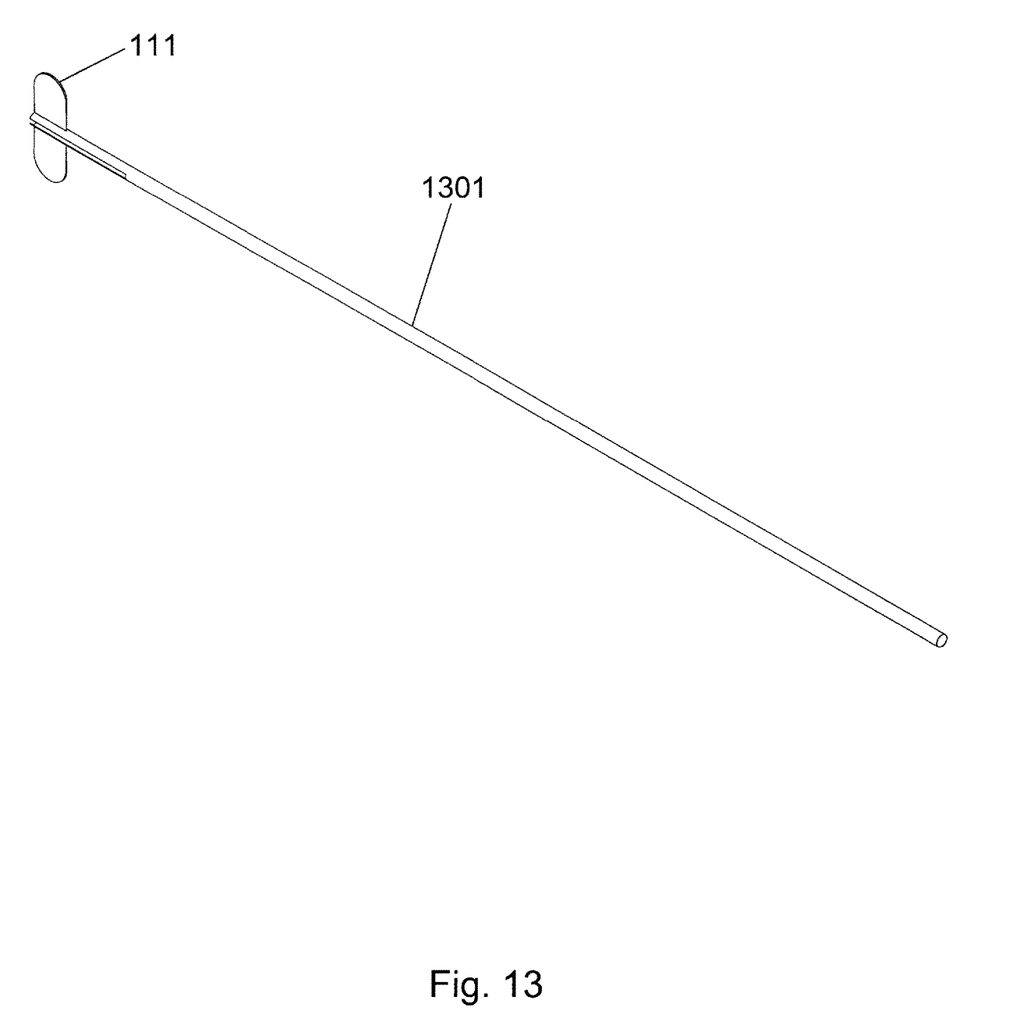
FIG. 13 is a perspective view of the drill bit extractor of the distal biceps tendon repair device.

FIG. 13 is a perspective view of the drill bit extractor of the distal biceps tendon repair device. A sleeve 1301 can be seen which fits within the bone drill guide 403 and allows the cannulated drill bit 113 to pass through. The sleeve 1301, as has been previously described, can be extended through the bone drill guide 403 so that it makes firm contact with the radius bone 199 as can be seen in FIG. 2, clamped or otherwise retained with the set screw 107 or other mechanical fixture such that the distal biceps tendon repair device 100 is firmly affixed to the radius bone 199 (see for example FIGS. 1 and 2) during surgical procedures, providing the surgeon with a stable and predictable working environment. Once the suture is placed through the drill bit cannula and circumferentially retrieved, the cannulated drill bit 113 must be removed either with a specialized drill such that the cannulated drill bit can be removed with the suture in place or with a manual drill bit extractor 111 such as depicted in FIG. 13. Such a manual drill bit extractor 111 fits onto the drill bit and has features such as wings or grips to allow the surgeon to manually rotate the cannulated drill bit 113 in a reverse direction and free it from the radius bone 199. The manual drill bit extractor 111 may have features such as slots, bevels, ridges, or other such engaging features to allow rotational force on the extractor to translate to rotation of the drill bit.

Figure 14:
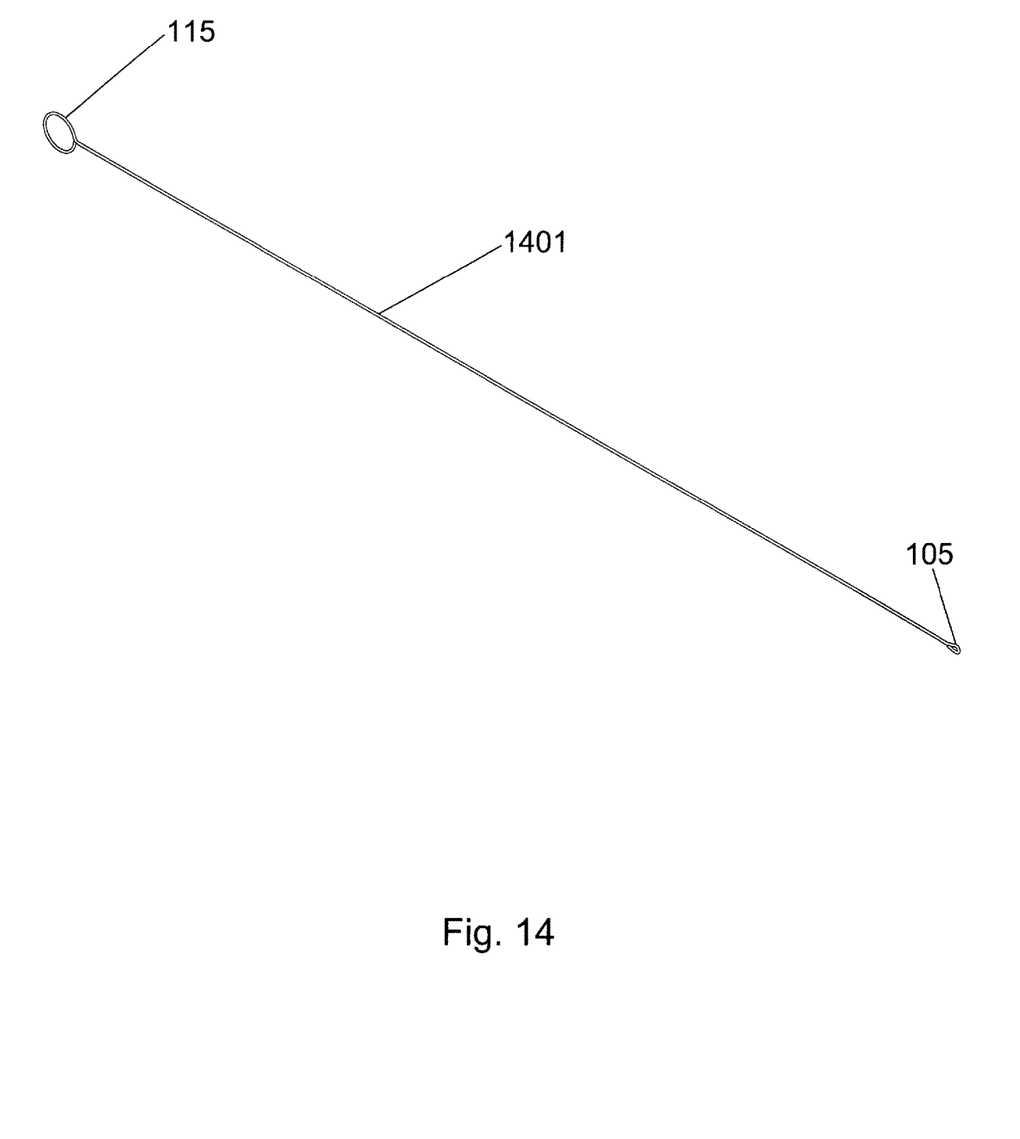
FIG. 14 is a perspective view of the suture guide of the distal biceps tendon repair device.

FIG. 14 is a perspective view of the suture guide 1401 of the distal biceps tendon repair device. The suture guide 1401 may comprise a suture or a wire or filament that can be used to guide a suture through the bone tunnel created by the cannulated drill bit and circumferentially around the radius bone to facilitate reattachment of the torn biceps tendon of the patient. In some embodiments of the present invention, the suture or suture guide 1401 has a suture loop 105 on the distal or patient end and a suture pull 115 on the proximal or surgeon end. The use of the suture/suture guide having been previously described herein.

Figure 15:
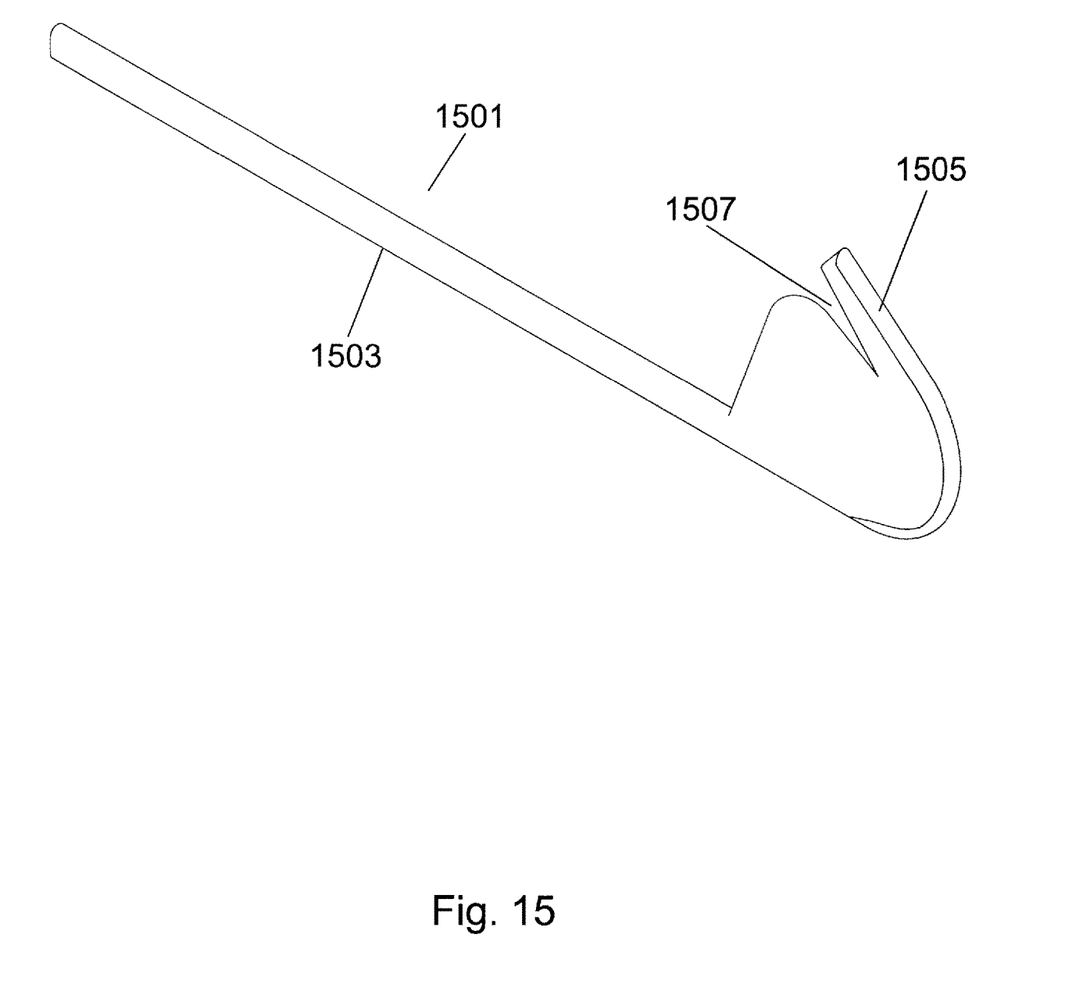
FIG. 15 is a perspective view of an alternate embodiment of a retrieval appendage of a retrieval wire of the distal biceps tendon repair device.

As previously stated, the retrieval wire may have a variety of retrieval appendages such as the Y shaped retrieval appendage 1101 depicted in FIG. 11, the purpose of which is to grasp and retain the suture or suture guide that has been inserted through the bone tunnel made by the cannulated drill bit of the present invention. FIG. 15 is a perspective view of an alternate embodiment of a retrieval appendage 1501 of a retrieval wire 1503 of the distal biceps tendon repair device. The retrieval appendage 1501 depicted in FIG. 15 comprises a retrieval hook 1505 and a retrieval notch 1507 where the retrieval notch becomes progressively narrower such that the retrieval notch 1507 can retain and capture the suture or suture guide in the v shaped narrow portion of the retrieval notch. While the retrieval appendage of FIG. 15 is another example of a retrieval appendage of the present invention, other such geometries such as j shaped hooks, barbs, clamps, jaws, or the like may also be employed.

The use of the distal biceps tendon repair device of the present invention having been previously described to repair biceps tendon tears, it is envisioned that the device of the present invention may also be useful for other surgical procedures that involve retrieval of sutures, guides, catheters, wires, or the like from a location that is not easily accessible or visible to the surgeon, or that involves surgical risk where the present invention can reduce such surgical risk through the stabilization and mechanical guidance and conformity provided by the present invention and the various embodiments described and envisioned herein.

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification and the attached drawings and claims.

What is claimed is:

1. A distal biceps tendon repair device comprising:
    a guide assembly comprising a proximal end, a distal end, a bone drill guide and a retrieval wire guide;
    a cannulated bone hook comprising a distal end, a proximal end and a hollow interior;
    the distal end of the guide assembly formed with the proximal end of the cannulated bone hook;
    the bone drill guide of the guide assembly having an entry at the proximal end of the guide assembly and an exit where the distal end of the guide assembly forms with the proximal end of the cannulated bone hook;
    the bone drill guide of the guide assembly capable of receiving a bone drill;
    the cannulated bone hook having a hollow interior that connects with the retrieval wire guide of the guide assembly to allow passage of a retrieval wire; and
    a bone drill stop coaxial with the bone drill guide and formed with the distal end of the cannulated bone hook.

2. The distal biceps tendon repair device of claim 1, further comprising a set screw threaded to the guide assembly.

3. The distal biceps tendon repair device of claim 1, wherein the bone drill stop is formed as a concave surface to receive and stop a bone drill.

4. The distal biceps tendon repair device of claim 1, wherein the bone drill stop has a suture passageway to allow a suture to pass through.

5. The distal biceps tendon repair device of claim 1, further comprising grips affixed to the guide assembly.

6. The distal biceps tendon repair device of claim 1, further comprising a cannulated bone drill bit.

7. The distal biceps tendon repair device of claim 6, wherein the cannulated bone drill bit further comprises a first marker and a second marker.

8. The distal biceps tendon repair device of claim 1, further comprising a manual drill bit extractor capable of engagement with a bone drill bit.

9. The distal biceps tendon repair device of claim 1, further comprising a retrieval wire capable of traversing the retrieval wire guide of the guide assembly and the hollow interior of the cannulated bone hook.

10. The distal biceps tendon repair device of claim 9, wherein the retrieval wire further comprises a retrieval wire pull.

11. The distal biceps tendon repair device of claim 9, wherein the retrieval wire further comprises a retrieval appendage.

12. The distal biceps tendon repair device of claim 11, wherein the retrieval appendage is a retrieval hook.

13. The distal biceps tendon repair device of claim 11, wherein the retrieval appendage is a retrieval notch.

14. The distal biceps tendon repair device of claim 1, further comprising a suture guide.

15. A distal biceps tendon repair device comprising:
    a guide assembly comprising a proximal end, a distal end, a bone drill guide and a retrieval wire guide;
    a cannulated bone hook that conforms to a radius bone of a patient; the cannulated bone hook comprising a distal end, a proximal end and a hollow interior;
    the distal end of the guide assembly formed with the proximal end of the cannulated bone hook;
    the bone drill guide of the guide assembly having an entry at the proximal end of the guide assembly and an exit where the distal end of the guide assembly forms with the proximal end of the capitulated bone hook;
    the cannulated bone hook having a hollow interior that connects with the retrieval wire guide of the guide assembly to allow passage of a retrieval wire; and
    a bone drill stop coaxial with the bone drill guide and formed with the distal end of the cannulated bone hook.

16. The distal biceps tendon repair device of claim 15, further comprising a retrieval wire capable of traversing the retrieval wire guide of the guide assembly and the hollow interior of the cannulated bone hook.

17. The distal biceps tendon repair device of claim 15, further comprising a cannulated drill bit.

18. A distal biceps tendon repair device comprising:
    guide assembly comprising a proximal end, a distal end, a bone drill guide and a retrieval wire guide;
    a cannulated bone hook that conforms to a radius bone of a patient; the cannulated bone hook comprising a distal end, a proximal end and a hollow interior;
    the distal end of the guide assembly formed with the proximal end of the cannulated bone hook;
    the bone drill guide of the guide assembly having an entry at the proximal end or the guide assembly and an exit where the distal end of the guide assembly forms with the proximal end of the cannulated bone hook;
    the cannulated bone hook having a hollow interior that connects with the retrieval wire guide of the guide assembly to allow passage of a retrieval wire;
    a bone drill stop coaxial with the bone drill guide and formed with the distal end of the cannulated hone hook;
    a retrieval wire capable of traversing the retrieval wire guide of the guide assembly and the hollow interior of the cannulated bone hook; and
    a cannulated drill bit.

19. The distal biceps tendon repair device of claim 18, further comprising a suture guide.

* * * * *

UNITED STATES PATENT AND TRADEMARK OFFICE
CERTIFICATE OF CORRECTION

PATENT NO. : 11,058,442 B2
APPLICATION NO. : 16/325387
DATED : July 13, 2021
INVENTOR(S) : Voloshin Page 1 of 1

It is certified that error appears in the above-identified patent and that said Letters Patent is hereby corrected as shown below:

In the Claims

Column 10, Line 41, Claim 18, 'at the proximal end or the guide assembly' should read -at the proximal end of the guide assembly- Signed and Sealed this
Twelfth Day of April, 2022

Drew Hirshfeld
*Performing the Functions and Duties of the
Under Secretary of Commerce for Intellectual Property and
Director of the United States Patent and Trademark Office*